United States Patent [19]
Gruenke

[11] Patent Number: 6,041,783
[45] Date of Patent: *Mar. 28, 2000

[54] INTEGRATED ACTIVITY SENSOR

[75] Inventor: Roger A. Gruenke, Overland Park, Kans.

[73] Assignee: Nellcor Puritan Bennett Corporation, Pleasanton, Calif.

[ * ] Notice: This patent is subject to a terminal disclaimer.

[21] Appl. No.: 08/471,582

[22] Filed: Jun. 7, 1995

[51] Int. Cl.[7] .................................................. A61B 5/103
[52] U.S. Cl. ............................................. 128/782; 128/774
[58] Field of Search .................................. 128/671, 672, 128/774, 782, 670, 677, 687, 667; 310/311, 330, 331, 369

[56] References Cited

U.S. PATENT DOCUMENTS

| | | | |
|---|---|---|---|
| 4,443,730 | 4/1984 | Kitamura et al. ........................ | 310/330 |
| 4,509,527 | 4/1985 | Fraden ..................................... | 128/671 |
| 4,802,485 | 2/1989 | Bowers et al. ........................... | 128/633 |
| 4,924,871 | 5/1990 | Honeyager .............................. | 128/672 |
| 5,055,671 | 10/1991 | Jones ...................................... | 128/667 |
| 5,311,875 | 5/1994 | Stasz ...................................... | 128/724 |
| 5,313,940 | 5/1994 | Fuse et al. .............................. | 128/687 |
| 5,406,952 | 4/1995 | Barnes et al. ........................... | 128/687 |
| 5,494,043 | 2/1996 | O'Sullivan et al. ..................... | 128/687 |

*Primary Examiner*—Michael Buiz
*Assistant Examiner*—Patrick W. Rasche
*Attorney, Agent, or Firm*—Fulwider Patton Lee & Utecht, LLP

[57] ABSTRACT

A motion transducer is embedded in a section of cable interconnecting a primary medical sensor with associated electronics. By affixing the section containing the transducer to a portion of a patient's anatomy, information relating to the parameter of primary concern as well as the patient's activity can be gathered without the complexity normally associated with instrumenting a patient for the acquisition of such data.

20 Claims, 1 Drawing Sheet

INTEGRATED ACTIVITY SENSOR

BACKGROUND OF THE INVENTION

The present invention generally relates to medical sensors and more particularly pertains to sensors that generate data indicative of a patient's movements or activity.

Patients are routinely monitored with respect to certain parameters that may be affected by the patient's activity. The effect may be the result of a physiological change resulting from such activity, a variation in the sensor/patient interface or some alteration of the signal after its generation and during transmission to the related instrumentation. It may therefore be most beneficial to have a record of the patient's activity to assist in interpreting data collected with respect to the parameter of interest. "Motion artifacts" can thereby be quickly identified, as can the data that is generated during periods of activity and periods of inactivity.

In testing patients for sleep disordered breathing and other sleep disorders it is frequently desirable to determine whether the patient is actually asleep. An EEG signal would of course readily facilitate a sleep-awake determination but such equipment is not always available. Alternatively, it has been found that a motion-detecting device fastened about the wrist area is quite an effective substitute as activity of the hand/wrist/arm is a fairly reliable indication of being awake.

Motion transducers for monitoring patient activity typically employ piezo-film material which generates an electrical signal when mechanically disturbed. Such material has heretofore been incorporated in for example a bracelet from which electrical leads extend to instrumentation where the generated signals are processed and recorded or otherwise made available for analysis.

Disadvantages associated with previously used activity sensors are inherent in the resulting multiplicity of the various sensors and wires extending from the "instrumented" patient. The complexity of such an array not only complicates the tasks of medical personnel but also encumbers the patient. Furthermore, some patients fear the presence of and the attachment to the various devices. As a result, it would be most desirable to reduce the apparent complexity of monitoring systems without sacrificing the quality and quantity of information gathered thereby.

SUMMARY OF THE INVENTION

The present invention provides a means for reducing the apparent complexity of the sensors and wiring array used in instrumenting a patient. More particularly, this is achieved by incorporating a motion transducer within a cable that interconnects any of a variety of sensors to instrumentation.

In treating certain sleep disorders, it may be desirable to simultaneously gather information relating to the blood oxygen saturation level as well as the patient's activity. An oximeter probe attached to the patient's finger necessarily has a cable extending therefrom that is typically routed along the hand and arm to the torso and on to the instrumentation. By embedding piezo-film in the cable in the area adjacent the wrist and routing the leads that extend therefrom through the same cable, a substantially simplified visual appearance results. The cable is secured to the wrist with tape or elastic bands to ensure that the slightest movement of the wrist causes a signal to be generated.

The present invention is adaptable to many other sensor combinations. In each iteration, the motion detector is incorporated in the cable interconnecting a primary sensor with the related instrumentation. The location of the piezo-film is selected to ensure its positioning adjacent to the body part the motion of which is of interest.

These and other features and advantages of the present invention will become apparent from the following detailed description of a preferred embodiment which, taken in conjunction with the accompanying drawings, illustrates by way of example the principles of the invention.

DETAILED DESCRIPTION OF THE INVENTION

Figure 1:
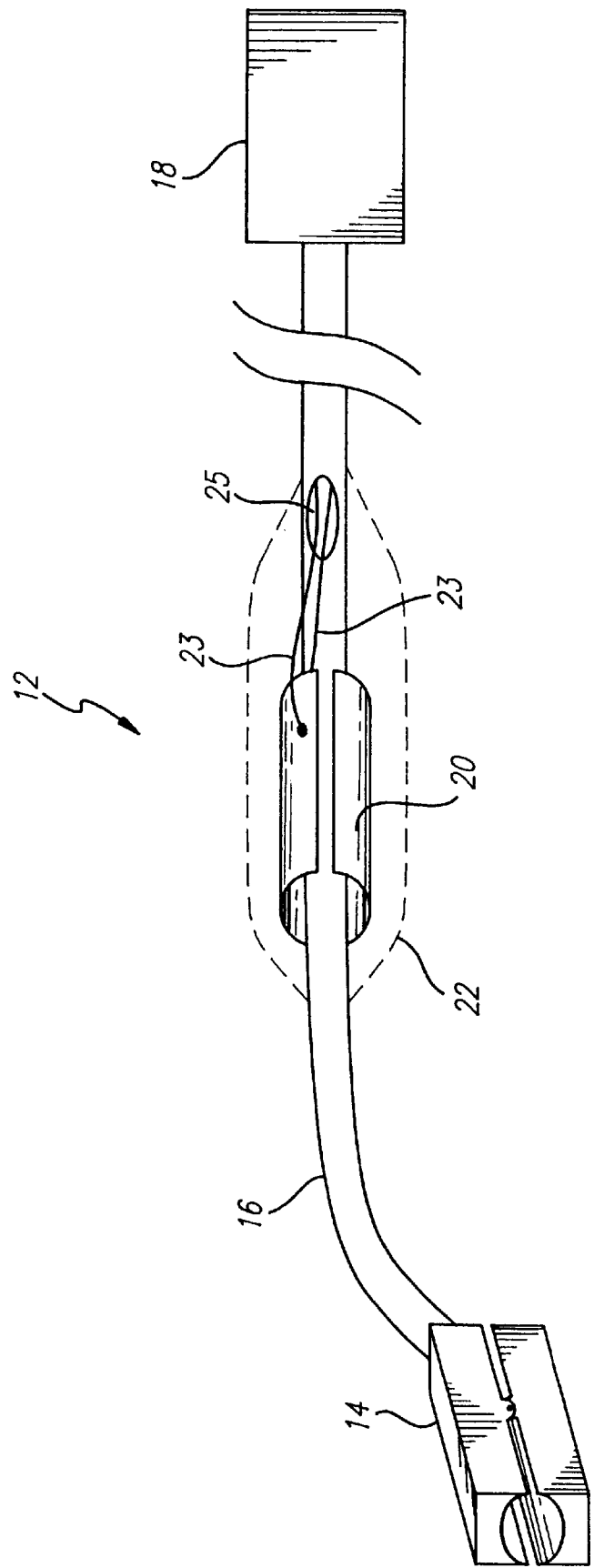
FIG. 1 is semi-schematic representation showing the integrated sensor of the present invention.

The present invention provides for the consolidation of an activity sensor with a primary medical sensor used to measure a particular medical parameter. The primary sensor is attached to the appropriate portion of a patient's anatomy, while a motion transducer is incorporated in the cable interconnecting the primary sensor with the related instrumentation. Information indicative of the patient's activity is thereby available for interpretation of the primary sensor data without the need to attach a separate sensor or route additional wiring.

The FIGURE illustrates a motion transducer incorporated in a cable extending from an oximeter finger probe. Such oximeters are well known in the art, and are operative to project beams of light through the finger and measure the intensity of the transmitted radiation. The wavelength of one of the beams of light is selected so as to be absorbable only by oxygen carrying hemoglobin while the second beam of light is not absorbed thereby. As a result, the relative intensities of the two beams provide an indication of the oxygen saturation level. The signal is however easily affected by any movement of the probe relative to the finger as different blood vessels are thereby caused to come under scrutiny. In order to be able to distinguish a real change in blood oxygen from a motion artifact it is therefore necessary to monitor the patient's movements.

The FIGURE shows a preferred embodiment of the present invention wherein the integrated system 12 includes an oximeter finger probe 14 that is interconnected via cable 16 to instrumentation 18 that amplifies, processes, displays or records the data. At a location along the cable which would be positioned adjacent the wrist area upon routing the cable from the patient's finger, along the arm to the torso and on to instrumentation 18, a section of piezo film 20 is wrapped about a section the cable. The piezo film 20 forms a cylindrical shape about a central axis of the cable 16. A preferred piezo film material is poly-vinylidine fluoride (PVDF). Two leads 23 extend therefrom and are routed into the cable at access port 25 to run the length of the cable to instrumentation 18. An outer sheath 22 covers the sensor 20 and wires 23 to provide a "single cable" appearance. The sheath may have a contrasting color or stenciling to demark the location of the sensor. It is preferred that the processing electronics for the motion transducer be incorporated in the same case that houses the oximeter electronics to further simplify the instrumentation.

In operation the oximeter finger probe 14 is clipped on to the patient's finger and the cable 16 is routed up along the arm to torso from where it connects to the instrumentation 18. The section of cable containing the motion transducer, which is axially distant from the oximeter finger probe 14, is positioned over the patient's wrist and adhesive tape or elastic bands are used on either side of the transducer containing section to affix the cable to the patient. Any relative movement across the wrist causes that section of cable to move or flex to mechanically disturb the piezo film, which causes an electric signal to be generated that is transmitted to electronics 18 for processing.

While a particular form of the invention has been illustrated and described, it will also be apparent to those skilled in the art that various modifications can be made without departing from the spirit and scope of the invention. More particularly, the activity sensor may be incorporated in any cable extending from the patient and consequently, integration with any number of medical sensors is possible. Additionally, any portion of the patient's body may be monitored for movement and any type of motion transducer may be used that is capable of being incorporated in the cabling. Accordingly, it is not intended that the invention be limited except by the appended claims.

What is claimed is:

1. An integrated sensor for monitoring a patient's activity, comprising:
   a primary medical sensor attachable to a patient's body;
   a cable interconnecting said primary sensor with associated electronics; and
   a motion transducer embedded in said cable at an axial distance from the primary medical sensor.

2. An integrated sensor for monitoring a patient's activity, comprising:
   a primary medical sensor attachable to a patient's body;
   a cable interconnecting said primary sensor with associated electronics; and
   a motion transducer embedded in said cable, wherein said motion transducer comprises piezo-film wrapped into a cylindrical form about a central axis of the cable and enclosed in an outer sheath.

3. The integrated sensor of claim 2 wherein said piezo-film material comprises PVDF.

4. The integrated sensor of claim 2 wherein said piezo-film has electrical leads extending therefrom that are routed into an interior of said cable to interconnect with associated electronics.

5. The integrated sensor of claim 1 wherein said primary sensor comprises an oximeter finger probe and said motion transducer is embedded in said cable at a location normally adjacent a preselected joint of said patient.

6. The integrated sensor of claim 5 wherein said preselected joint comprises a wrist of said patient.

7. The integrated sensor of claim 5 wherein said motion transducer comprises piezo-film wrapped into a cylindrical form about a central axis of the cable and enclosed in an outer sheath.

8. The integrated sensor of claim 7 wherein said piezo-film comprises PVDF.

9. A method for monitoring a patient's activity, comprising the steps of:
   attaching a medical sensor to said patient wherein said sensor is interconnected to electronics via a cable;
   incorporating a motion transducer within a preselected portion of said cable at an axial distance from the medical sensor; and
   affixing said preselected portion of said cable to a preselected area of said patient, whereby movement of said area is indicative of patient activity.

10. The method of claim 9 further comprising the step of routing leads extending from said motion transducer through said cable to electronics capable of processing any signals generated thereby.

11. The method of claim 9 wherein the preselected area of said patient comprises a joint.

12. The method of claim 11 wherein the joint comprises a wrist of said patient.

13. The method of claim 9 wherein the medical sensor comprises an oximeter finger probe, the motion transducer comprises piezo film, and the preselected area of said patient comprises a wrist joint of said patient.

14. An integrated sensor for monitoring a patient's activity, comprising:
   a primary medical sensor attachable to a patient's body;
   a cable interconnecting said primary sensor with associated electronics; and
   a motion transducer positioned along the cable between the primary sensor and the associated electronics, said motion transducer being positioned at an axial distance from the primary medical sensor.

15. The integrated sensor of claim 14, wherein the primary medical sensor comprises an oximeter finger probe, and the motion transducer is positioned on the cable at an axial distance sufficient to permit the motion transducer to be positioned adjacent a wrist area of the patient while the oximeter finger probe is clipped to a finger of the patient.

16. The integrated sensor of claim 14, wherein the motion transducer comprises piezo film.

17. The integrated sensor of claim 16, wherein the cable has a central axis, and the piezo film is wrapped into a generally cylindrical shape about the cable axis.

18. The integrated sensor of claim 17, further comprising an outer sheath enclosing the piezo film.

19. The integrated sensor of claim 18, further comprising indicia on the outer sheath denoting the location of the motion transducer.

20. The integrated sensor of claim 16, wherein the piezo film comprises PVDF.

* * * * *